United States Patent [19]

Bussiere et al.

[11] 4,168,447
[45] Sep. 18, 1979

[54] PRESTRESSED CYLINDRICAL PIEZOELECTRIC ULTRASONIC SCALER

[76] Inventors: Ronald L. Bussiere, 1030 Carol Way; William D. Adams, 1027 Carol Way, both of Edmonds, Wash. 98020

[21] Appl. No.: 893,969

[22] Filed: Apr. 6, 1978

Related U.S. Application Data

[63] Continuation of Ser. No. 772,328, Feb. 25, 1977, abandoned, which is a continuation of Ser. No. 666,787, Mar. 15, 1976, abandoned.

[51] Int. Cl.² .......................................... H01L 41/10
[52] U.S. Cl. .............................. 310/316; 32/DIG. 4; 310/323; 310/325
[58] Field of Search ............... 310/322, 323, 325, 334, 310/316, 26; 32/DIG. 4, 50, 58; 318/116, 118

[56] References Cited

U.S. PATENT DOCUMENTS

| | | |
|---|---|---|
| 3,210,580 | 10/1965 | Bodine, Jr. .......................... 310/325 |
| 3,230,403 | 1/1966 | Lewis ............................... 310/325 X |
| 3,432,691 | 3/1969 | Shoh ................................... 310/316 |
| 3,518,766 | 7/1970 | Burt .................................. 310/325 X |
| 3,651,352 | 3/1972 | Puskas ................................. 310/316 |
| 3,809,977 | 5/1974 | Balamuth ......................... 310/325 X |
| 3,924,335 | 12/1975 | Balamuth ......................... 310/325 X |
| 3,934,526 | 1/1976 | Damast et al. .................... 310/323 X |

Primary Examiner—Mark O. Budd
Attorney, Agent, or Firm—Dowrey & Cross

[57] ABSTRACT

The scaler includes a transducer and an energizing circuit. The transducer includes a tubular piezoelectric transducer element which is maintained in compressive stress when energized by an axial tension bolt adapted to mount a vibratory work tool. The energizing circuit drives the transducer element at its resonant frequency and maintains resonant frequency within an optimum band width, despite changes in capacitive reactance of the transducer element produced by torque applied thereto as the work tool is pressed against an object. A fluid delivery system delivers fluid to the work tool via the tension bolt to effect scaling.

9 Claims, 4 Drawing Figures

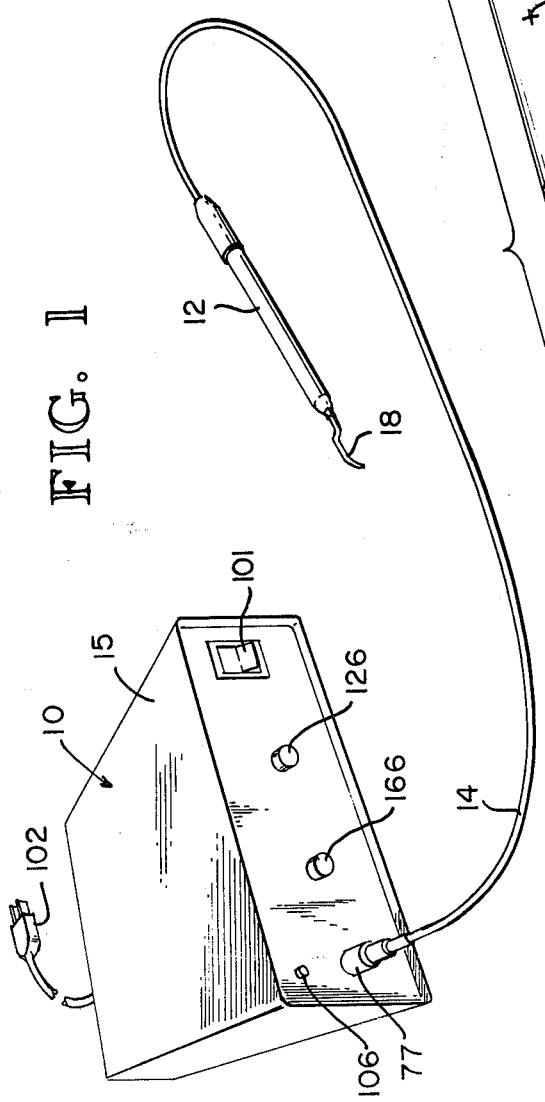
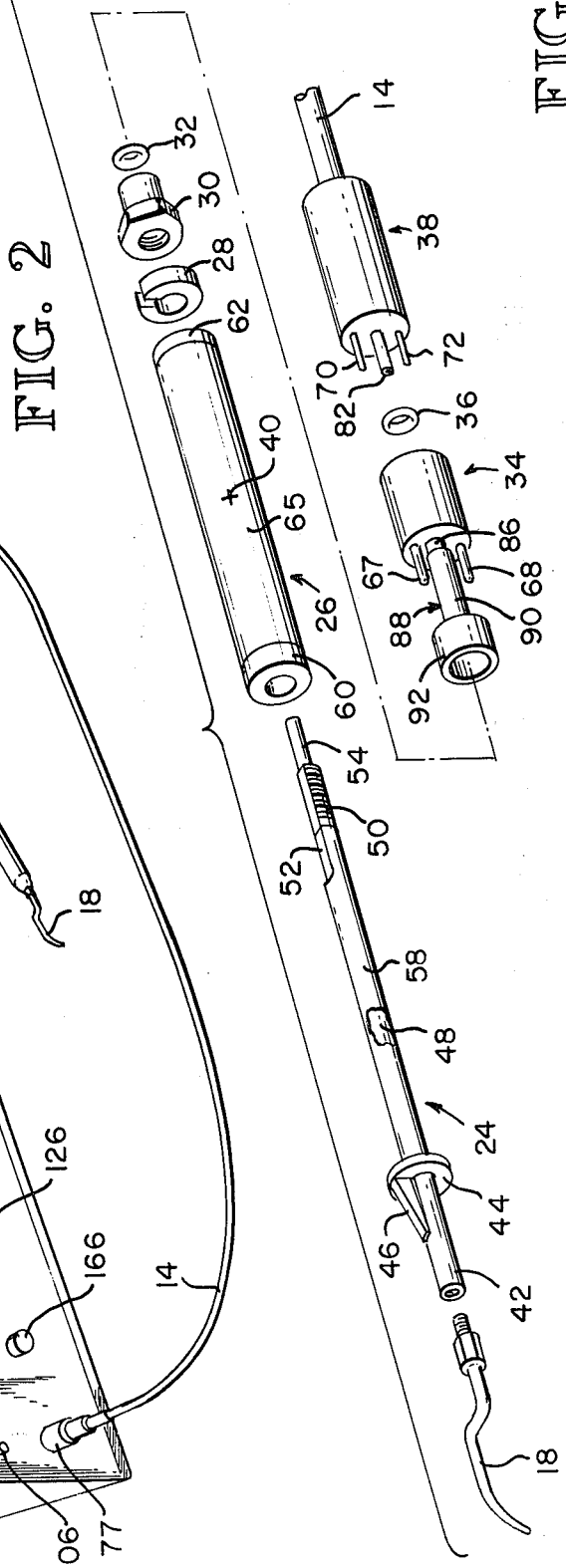
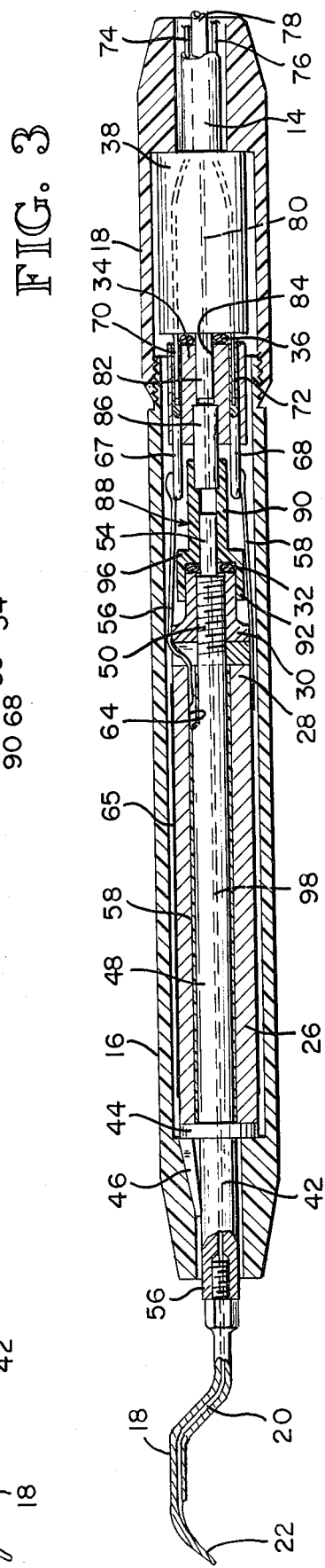

PRESTRESSED CYLINDRICAL PIEZOELECTRIC ULTRASONIC SCALER

This is a continuation, of application Ser. No. 772,328, filed Feb. 25, 1977, which is a continuation of Ser. No. 666,787 filed Mar. 15, 1976, both now abandoned.

BACKGROUND OF THE INVENTION

This invention relates to ultrasonic systems. One particular application of this invention as an ultrasonic scaler is illustrated and described herein; however, the invention, in its broadest form, is not limited to an ultrasonic scaler and may be utilized in other applications and environments.

Ultrasonic scalers and ultrasonic systems in general typically include magnetostrictive or piezoelectric transducer elements for converting an ultrasonic frequency electrical signal, preferably corresponding to the resonant frequency of the transducer, into ultrasonic frequency vibrations which are applied to a work tool. Magnetostrictive transducers tend to overheat and have a relatively low temperature Curie point and, therefore, are undesirable for scaler and similar applications which require prolonged operation. In many scaler applications, magnetostrictive transducers heat up rapidly, thus causing discomfort to the patient, and quickly reach their Curie point, at which they cease operating. Consequently, scalers equipped with magnetostrictive transducers must be operated infrequently, or in short intervals, and allowed to cool down before they can be used again. Piezoelectric transducers, on the other hand, do not tend to overheat and possess a relatively high temperature Curie point. For these and other reasons, piezoelectric transducers now offer the most economical and effective transducers for scaler and similar applications.

Prior piezoelectric transducers typically include two or more disc-shaped piezoelectric crystals (see U.S. Pat. No. 3,809,977), or a single tubular crystal (see U.S. Pat. Nos. 3,522,801 and 3,645,255). Disc crystals provide a relatively weak, or low powered, transducer. For this reason, at least two disc crystals are necessary in most practical cases in order to obtain acceptable power levels. Multiple disc crystals, of course, increase the complexity of the crystal mounting and vibration transmitting structure and, hence, decrease reliability of the transducer. In the transducer disclosed in the U.S. Pat. No. 3,809,977, for example, at least two disc crystals are energized in parallel by a common electrode and supported by at least three threadably connected components. Additionally, disc crystals are highly sensitive to applied torque, the capacitance thereof changing substantially in response to torque applied to the crystal by the work tool as the latter contacts and is pressed against an object (e.g., a tooth). Disc crystals, therefore, when energized by a circuit particularly sensitive to changes in capacitance (i.e., a high inductive to capacitance ratio, see U.S. Pat. No. 3,596,206), display a rapid decline in vibration frequency from resonant frequency when pressure is applied to the work tool. As the crystal vibration frequency drops off from resonant frequency, of course, the crystal is energized in a much less efficient manner, and the power soon drops off, with concomitant increase in heating. To bring the crystal power back up to an acceptable level, however, it is then necessary to increase the level of electrical power applied to the crystal, thereby producing further undesirable heating.

Although tubular piezoelectric crystals offer to overcome or substantially mitigate these and other disadvantages of disc crystals by providing greater vibration amplitudes, power levels, etc., prior transducers equipped with tubular crystals, such as those disclosed in U.S. Pat. Nos. 3,522,801 and 3,645,255, are prone to failure. Tubular crystals tend to fracture or overheat as destructive tensile stresses accumulate within the crystal when energized. Disc crystals, of course, also tend to fracture or overheat for similar reasons; however, as a practical matter, disc crystals are not operated at power levels and vibration amplitudes comparable to tubular crystals and, hence, they have not experienced the failure problems of tubular crystals in most practical transducer applications. Until this invention, therefore, it has been necessary to sacrifice the superior power levels, vibration amplitudes, etc., offered by tubular crystals for the reduced tendency to fracture or overheat of disc crystals, while tolerating their operating deficiencies.

SUMMARY OF THE INVENTION

This invention provides an ultrasonic system which includes a transducer made up of a tubular piezoelectric transducer element in combination with means for maintaining compressive stress in the element when energized by appropriate energizing means.

According to one preferred embodiment of the invention particularly suited for scaler and similar applications, the transducer includes a single member extending axially through the transducer element for applying compressive forces to the ends of the element, the compressive forces being of sufficient magnitude to continuously maintain a compressive stress in the element when energized. This member further serves to transmit vibrational forces directly to a vibratory work tool, and may include a longitudinal fluid passage for delivering fluid to the work tool.

The preferred energizing means of this invention include a resonant circuit, in which the transducer element acts as the capacitive element, and an oscillator circuit responsive to changes in capacitive reactance of the transducer element for driving the resonant circuit and maintaining a desired frequency corresponding to the resonant frequency of the element. The oscillator circuit includes timed feedback means for producing a feedback voltage in response to changes in capacitive reactance of the transducer element caused, for example, by application of torque thereto as the work tool is pressed against an object (e.g., a tooth). This feedback voltage modifies a predetermined reference voltage to control the oscillator, and hence the frequency at which the resonant circuit is driven thereby. Thus, the oscillator circuit, by modifying a reference voltage with a timed feedback voltage, is able to respond to relatively small changes in capacitive reactance.

Thus, it will be appreciated from the foregoing summary that this invention solves problems of fracturing and overheating heretofore associated with tubular piezoelectric crystals to yield operational efficiency, power levels and endurance heretofore beyond the reach of prior ultrasonic systems, transducers and energizing means. The transducer of this invention provides prolonged operation at substantially constant power levels, without undesirable heating, as well as provides a highly effective work tool vibration pattern. Furthermore, unlike disc transducer elements, the tubular transducer element of this invention is relatively insensitive to applied torque, and the resonant circuit is likewise relatively insensitive to changes in capacitance, so that variations in frequency of the resonant circuit produced by changes in capacitive reactance of the transducer element are of relatively small magnitude. The ultrasonic frequency electrical signal applied to the transducer element, therefore, may be maintained within narrow limits with respect to its resonant frequency to achieve operation at optimum band width (Q). Thus, the transducer may be operated in a highly efficient manner, to yield substantially constant power levels without overheating when the work tool is pressed against an object (e.g., a tooth), even with considerable force. Additional cooling, of course, may be provided in scaler and similar applications by passing a fluid, preferably water, through the axial transducer member to the work tool—the fluid cooling the transducer, the work tool and the tooth. In most practical applications, a single tublar piezoelectric crystal provides sufficient power levels; however, two or more crystals may be positioned end to end in some instances, provided a compressive stress is maintained therein when energized.

These and other features, objects and advantages of the present invention will become apparent in the detailed description and claims to follow taken in conjunction with the accompanying drawings in which:

BRIEF DESCRIPTION OF THE DRAWINGS

FIG. 1 is a perspective view of the ultrasonic system of this invention;

FIG. 2 is a perspective assembly view of the transducer of the FIG. 1 system;

FIG. 3 is a longitudinal section of the transducer of the FIG. 1 system;

DETAILED DESCRIPTION OF THE DRAWINGS

Figure 4:
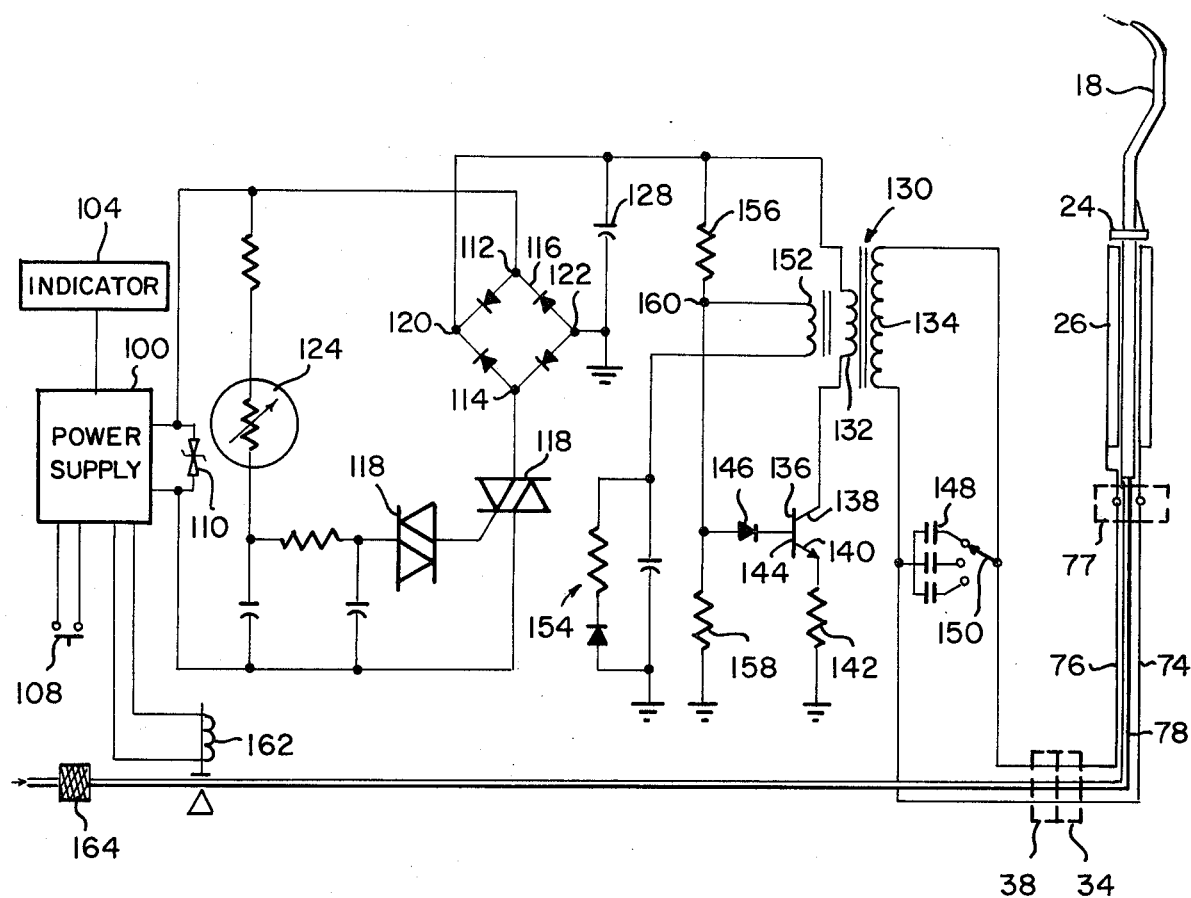
FIG. 4 is a circuit schematic of the energizing and fluid delivery circuit of the FIG. 1 system.

The ultrasonic scaler of FIG. 1 includes a control unit 10 and a transducer 12 connected thereto by a combination electrical power and fluid delivery cable 14. The control unit includes appropriate electronic energizing circuitry, fluid delivery circuitry, manual controls, and indicators—all contained within a housing 15. The electronic and fluid circuitry, manual controls, and indicators will be described presently with specific reference to FIG. 4.

The transducer of FIG. 1 includes a sectional housing, the front and rear (left and right, as illustrated) sections of which are shown threadedly connected and designated by reference numerals 16 and 18 in FIG. 3. The housing is of appropriate configuration, preferably tubular with front and rear tapered end surfaces, for hand held usage. The power/fluid cable 14 is received at the rear end of the housing. A tip 18 or equivalent vibratory work tool is detachably mounted at the front end of the housing. In the example, the tip includes an internal fluid passage 20 for delivering water to a distal tip portion 22 (FIG. 3). The illustrated tip, therefore, is adapted for scaling. The choice of tip or work tool, of course, depends upon the particular application, and other tips or work tools of different construction may be substituted for the illustrated tip, if desired.

The transducer of FIG. 1 is depicted in FIG. 2 in partially disassembled condition, and in FIG. 3 in assembled condition. Referring first to FIG. 2, the transducer includes, proceeding from front to rear (or left to right), a single elongated tension bolt 24, a tubular piezoelectric transducer element 26, a reaction mass 28, a nut 30, a forward O-ring 32, a female electrical/fluid coupling section 34, a rear O-ring 36, and a male electrical/fluid coupling section 38. The housing and electrical leads are not shown in FIG. 2.

The transducer element 26 is comprised of a tubular piezoelectric crystal, preferably lead zirconate titanate, for converting an ultrasonic frequency electrical signal into ultrasonic frequency mechanical vibrations in a known manner. The crystal is of a certain length selected to resonate at a desired ultrasonic frequency and optimum band width (Q) for maximum efficiency. If the crystal is shorter or longer than this certain length, it is not possible to achieve optimum band width. The design and selection of crystal length, as well as wall thickness, material, etc., will be apparent to one of ordinary skill in the art.

The crystal, when energized by means described hereinafter, vibrates primarily in an axial direction, the axial vibrational forces being transmitted by the tension bolt 24 to the tip 18, as will be described presently. The crystal, of course, also vibrates in a radial direction; however, these radial vibrations are of relatively small magnitude compared to the axial vibrations and are not utilized, although the inner surface of the adjacent housing section 16 is of sufficient diameter to accommodate the radial vibration component. All reference hereinafter to crystal vibrations, therefore, will relate to the axial vibration component.

Axial vibration of the crystal occurs in opposite directions with respect to a nodal point located about midway along the length of the crystal and referenced by numeral 40 in FIG. 2. When energized, the crystal expands axially in the tensile direction approximately twice the distance it contracts in the compression direction with respect to the nodal point 40. Inasmuch as the strength of the ceramic material which makes up the crystal is greater in compression than in tension, however, the crystal would soon fracture, or develop destructive heat, because of this imbalance in tensile and compressive stresses produced during axial vibration thereof. Accordingly, this invention maintains the crystal under compressive stress when energized by continuously applying opposed axial compressive forces to the ends of the crystal of sufficient magnitude to cancel out tensile stress produced during axial expansion in the tensile direction. Thus, the crystal is maintained under compressive stress when energized, the crystal stress varying between zero and a compressive stress of about twice the tensile stress amplitude which would be experienced if the crystal ends were unrestrained. Thus, it is possible, by maintaining a compressive stress in the crystal when energized, to prevent fracturing of the crystal material, as well as minimize or substantially eliminate overheating. Overheating is further minimized by operating the transducer in a highly efficient manner at optimum band width (Q), as will be described presently.

Compressive stress is maintained in the crystal when energized by the tension bolt construction illustrated in FIGS. 2 and 3. A single tension bolt extends axially through the crystal. The bolt is made up of material adapted to withstand cracking, fatigue and related failure phenomena produced by crystal vibration while under a tensile load sufficient to maintain compressive stress in the crystal. The bolt includes a forward end portion 42 (left end portion as illustrated) which terminates in an internally threaded end adapted for direct threaded connection with the tip, as shown (FIG. 3). A thrust collar 44 projects radially from the other end of portion 42, collar 44 being integral therewith. A tapered key 46 projects forwardly from the collar in appropriate disposition for engagement with a mating keyway formed by the housing section 16 in order to prevent rotative shifting therebetween and, hence, between the entire tension bolt assembly and the housing, when assembled. The midportion 48 of the bolt is of an outer diameter corresponding to that of the forward end portion and fits at close clearance with the inner surface of the crystal when assembled, as shown (see FIG. 3). The bolt terminates at its rear end portion in an externally threaded portion 50 of semicircular outline which includes a relief surface 52, and a rear end portion 54 of cylindrical outline and reduced diameter. The forward end portion, collar, key, midportion, threaded portion, and rear end portion are of integral construction. A slotted ring-shaped reaction mass 28 of appropriate high density material is fitted over portion 50 with its slot in axial alignment with the relief surface 52 to allow passage of an electrical lead 56 operatively connected with the inner surface of the crystal for energizing the crystal as will be described presently. The reaction mass is held firmly against the rear end of the crystal by the nut 30 threaded upon portion 50. The outer surface of the nut is spaced radially from the inner surface of the housing section 16 to allow passage of lead 56 and a second lead 58 therearound, as shown (FIG. 3). The crystal is maintained in compressive stress when energized by tightening the nut 30 with sufficient torque that the axial compressive forces applied to the crystal by the collar 44 and nut 30 via the reaction mass 28 corresponds to approximately twice the tensile stress amplitude of the crystal.

When energized, therefore, the crystal will vibrate axially with respect to nodal point 40 while remaining in compressive stress, and the tension volt 24 will transmit such vibration directly to the tip 18 via forward portion 42. The bolt, preferably, is so constructed and arranged with respect to crystal length, vibration amplitude, etc., that it provides linear acoustic vibration transmittance to the work tool with minimum adverse influence upon resonant vibration of the crystal. To this end, the bolt should be as long as possible to contribute minimum stiffness to the composite crystal-bolt assembled structure, and the forward portion 42, or the portion directly connected with the tip, should project from the adjacent end of the crystal a greater distance than the rear portion 50, or the portion opposite the tip. The reaction mass acts as a bulkhead against which rearwardly directed vibrational forces bounce off and are redirected as an acoustical cone in a forward direction toward the tip. The threaded bolt/tip connection, of course, provides positive vibrational coupling between the crystal and tip.

The bolt further is so constructed and arranged with respect to the crystal and tip that a second nodal point, referenced by numeral 56 in FIG. 3, is established adjacent the threaded connection between the tip and forward portion 42 by selecting an appropriate length for the forward portion 42. The establishment of nodal point 56 prevents or substantially reduces the tendency of the tip to unscrew during operation. The length of forward portion 42 is further selected so that the vibrating portions thereof adjacent nodal point 56 vibrate in proper phase with the tip and crystal. Thus, vibrational energy reflected back from the tip in a rearward direction will not have an adverse effect upon crystal vibrations. The actual selection of appropriate specific bolt dimensions, of course, will be understood by one of ordinary skill in the art by referring to the teachings of this invention. In the example of FIGS. 2 and 3, the crystal and tension bolt of this invention for scaler applications are depicted in approximate proportions to achieve optimum band width vibration at a resonant frequency of about 25,000 cycles per second.

Electrical power is applied to the crystal by inner and outer electrode layers 64 and 65 made up of electrically conductive material deposited upon the inner and outer cylindrical crystal surfaces, except for the unmasked end portions 60 and 62. These layers constitute opposed electrodes by which the crystal is energized. It will be appreciated at this point that, by virtue of the illustrated crystal construction, the opposed layers and the crystal constitute a capacitive element, the layers constituting opposed electrodes and the crystal constituting a dielectric. The significance of this construction will become apparent in the description to follow.

The bolt is isolated electrically from the crystal and energizing means to prevent undesirable static charges, which otherwise might be tapped from the crystal energizing circuit, from developing at the distal end of the tip. Referring again to FIGS. 2 and 3, the portion of the bolt adapted to fit axially within the crystal is surrounded by a sleeve 55 of a length corresponding to the length of the crystal. The sleeve is composed of a suitable dielectric material, such as Teflon, and is of sufficient thickness to prevent transmittance of a static charge from the crystal electrodes to the bolt and thence to the tip. Likewise, the end portions 60 and 62 (FIG. 2) of the crystal are unmasked to prevent transmittance of a static charge from the ends of the electrodes to the bolt.

Electrical power is applied to the crystal via two electrical leads 56 and 58 respectively secured at diametrically opposed locations to the inner and outer layers 64 and 65, as shown (FIG. 3). Although these leads could be secured to layers 64 and 65 at other locations, the illustrated lead connections are preferred because they further minimize development of static charge during crystal operation. In the example, the leads are further secured to the crystal at locations spaced from the adjacent end of the crystal, the adjacent uncovered portion 62 thus further providing electrical insulation with respect to the overlying portions of the leads.

The remaining components of the transducer mentioned briefly with respect to FIG. 2 will now be described in detail with specific reference to FIGS. 2 and 3. The female electrical/fluid coupling section 34 includes two pin connectors 67 and 68 respectively connected electrically with the rear ends of leads 56 and 58. The rear ends of these connectors, in turn, provide detachable electrical connection with coaxially insertable connectors 70 and 72 of the male electrical/fluid coupling section 38. The cable 14 includes two electrical conductors 74 and 76 which terminate at the connectors 70 and 72 for transmission of electrical current from the control unit to the transducer. A second set of male/female coupling sections 77 may be provided at the control unit 10 (see FIG. 1) to allow the detachable connection of the other end of the cable with unit 10.

Thus, the transducer, cable, or control unit may be disconnected for servicing, replacement, shipping, etc., by detachment of the appropriate male/female couplings.

As a scaler, the transducer also delivers an appropriate scaling fluid, preferably water, to the tip, the fluid being delivered to the rear end of the transducer via a fluid line 78 which is incorporated in the cable. To this end, the male section 38 includes an axial fluid passage 80 which terminates in an external fluid conduit 82 adapted to be inserted into a mating axial bore 84 in the female section 34. The walls of conduit 82 and the bore 84 are formed to frictionally engage one another so as to establish a fluid seal; however, for a more reliable seal, O-ring 36 may be provided between the opposed faces of the sections 34 and 38. The bore 84 terminates adjacent a second external conduit 86, the forward end of which is surrounded by a combination fluid delivery and shock absorbing member 88 of tubular construction. The member 88 includes a reduced diameter rear portion 90 which surrounds and is fixed with respect to the forward end of conduit 86. Member 88 further includes an enlarged diameter forward portion 92 which surrounds and engages the rear tubular portion of bolt 30. The O-ring 32 is positioned between the rear end of bolt 30 and a shoulder 96 (FIG. 3) formed between the forward and rear portions of member 88. This O-ring provides a fluid seal between the bolt and member 88 and additionally serves as a shock absorbing element for absorbing vibrational forces between the tension bolt construction and the transducer electrical and fluid delivery components located to the rear thereof (or to the right as illustrated in FIG. 3). Finally, the bolt includes an axial fluid passage 98, depicted in broken lines in FIG. 3, which extends between the ends thereof and communicates at its forward end with the tip passage 20 for delivery of fluid thereto. It will be recognized that sections 34 and 38 further provide a detachable connection between the various fluid passages in a manner generally similar to the detachable electrical connections described previously.

Referring now to FIG. 4, the energizing circuit of this invention includes a power supply 100 for receiving alternating current electrical power via a suitable power connector 102 (FIG. 1). The power supply is turned off and on by a suitable power switch 101 (FIG. 1). The power supply operates an appropriate power indicator 104, the indicator constituting, for example, a light 106 mounted on the front face of the FIG. 1 housing. The power supply is controlled by a foot pedal 108 and powers the transducer energizing circuit, as well as controls a fluid delivery circuit, all depicted schematically in FIG. 4. The transducer of FIGS. 1–3 is depicted schematically in FIG. 4, as are electrical lines 74, 76 and connectors 34, 38, 77.

The energizing circuit includes a power circuit, an oscillator circuit, and a resonant circuit. The power circuit is made up of a thiractor 110 for suppressing voltage transients present in alternating current received from the power supply. Alternating current from the thiractor is then applied to opposed terminals 112 and 114 of full wave rectifier bridge 116. A phase angle firing circuit made up of two series connected triacs 118 phase angle fires alternating current to the bridge at terminal 114 so that the output of the bridge, which appears at opposed terminals 120 and 122, is pulsating direct current. A potentiometer 124, actuated by a suitable external control knob 126 (FIG. 1), controls the power level of the alternating current electrical power applied to bridge 116. The pulsating direct current which appears at bridge terminals 120 and 122 is filtered by a capacitor 128 and then is applied to the oscillator circuit.

The oscillator circuit controls operation of a transformer 130, preferably a three-winding transformer, which includes windings 132 and 134 for inductively coupling the oscillator and resonant circuits. Preferably the transformer is of a toroidal configuration which provides maximum efficiency and reduced hysteresis losses at high frequency, although other types of transformers may be used, if desired. The inductive coupling provided by windings 132 and 134 is controlled by a transistor 136 having its collector 138 connected in series with winding 132 and its emitter 140 connected to ground via a resistor 142. The conductive or non-conductive condition of the transistor is controlled by applying a controlled base voltage to its base 144 via a diode 146, the base voltage being controllable by feedback means to be described presently. It will be recognized that, by inductively coupling the oscillator and resonant circuits by means of windings 132 and 134, the transducer of FIGS. 1–3 will be isolated electrically from the power and oscillator circuits, thereby minimizing or substantially eliminating the possibility that an electrical shock might be transmitted from these circuits to the transducer.

Referring now to the resonant circuit of FIG. 4, winding 134 and the piezoelectric crystal (and its associated electrode layers) respectively constitute the inductive and capacitive elements of the resonant circuit, the frequency of which will therefore vary in response to dynamic or static variation in capacitive reactance of the crystal. For most efficient operation of the crystal, however, it is desirable to operate it at or near its resonant frequency over an optimum band width (Q) as narrow as possible. To compensate for static changes in capacitive reactance produced, for example, by variation in wall thickness of the crystal, a second capacitive element 148 may be connected selectively in parallel with the crystal. This second capacitive element thus shares voltage with the crystal during oscillation of the resonant circuit and effectively cancels variation in capacitive reactance produced by varying wall thickness so that the resonant circuit will oscillate at resonant frequency. A switch 150 may be provided for selectively connecting one of a plurality (e.g., three) of capacitive elements in parallel with the crystal, the respective capacitances of which represent appropriate compensation for variations in capacitive reactance produced by manufacturing tolerances of the particular crystal used.

The oscillator circuit includes feedback means responsive to dynamic changes in capacitive reactance of the crystal (e.g., changes produced by application of torque to the crystal) for maintaining resonant frequency. The feedback means of the FIG. 4 oscillator include a third transformer winding 152 which is inductively coupled with winding 132 and connected to ground via a timing network 154. The feedback winding senses dynamic impedance changes produced by load or torque applied to the crystal and automatically increases the oscillator frequency in the oscillator circuit. The feedback winding produces a feedback voltage which is applied to and controlled by the timing network in accordance with the desired oscillation frequency (i.e., the crystal resonant frequency) to arrive at a timed feedback voltage. The timed feedback voltage is then applied via diode 146 to the base 144 for controlling operation of the transformer. In this way, the crystal is energized in a highly efficient manner, the crystal power level remaining constant merely by appropriate adjustment of the oscillator frequency during dynamic changes in capacitive reactance, without having to increase power level.

In addition to controlling the oscillator frequency to maintain resonant frequency, the oscillator and resonant circuits of FIG. 4 in combination with the illustrated tubular crystal structure of this invention further operate the crystal at optimum band width (Q). By virtue of the tubular crystal structure, the inductance to capacitance ratio of the FIG. 4 resonant circuit is relatively small; therefore, it is relatively insensitive to dynamic changes in capacitance. Furthermore, the tubular crystal structure is likewise less sensitive to applied torque than disc crystals, for example. Thus, torque produced frequency variations in the resonant circuit are of relatively small magnitude so that the frequency adjustments which must be performed by the oscillator circuit in order to compensate for impedance changes are not as severe in the present invention as in the case of disc crystals, or conventional oscillator circuits having high inductance to capacitance ratios. This results in much finer control of crystal frequency and, hence, more efficient crystal operation at optimum band width (Q).

The feedback means of this invention are further sensitive to such small variations in capacitive reactance. A voltage divider including resistors 156 and 158 establishes a predetermined reference voltage at point 160. This voltage is modified by adding or subtracting the timed feedback voltage produced by the feedback winding and timing network and then is applied to the base 144. In this way, the oscillator circuit is able to respond to relatively small changes in capacitive reactance and, hence, to control oscillator frequency in a precise, highly effective manner.

The fluid delivery system of FIG. 4 includes a solenoid actuated control valve 162, the solenoid being controlled by the power supply in response to actuation of the foot pedal. An appropriate filter 164 may be positioned upstream of the valve 162 to filter contaminants or solids from the water provided by a water supply (not shown). The volume of water, of course, may be varied or controlled by another flow control valve (not shown) located upstream of valve 162 and controlled by a panel mounted control knob 166 (FIG. 1). The fluid delivery system feeds water via the combination electrical and fluid delivery cable, depicted schematically in FIG. 4, to the transducer and thence to the tip as described previously. The detachable connectors, of course, also serve to disconnect the fluid delivery system from the transducer to permit replacement or substitution of the cable, the transducer, or both, as mentioned previously.

As a scaler, the ultrasonic system of this invention provides highly effective removal of plaque, tartar and similar substances from the teeth surfaces and, with respect to dental applications in general, may find additional uses, such as removal of cement from teeth undergoing orthodontia treatment. In the removal of plaque or tartar, for example, the transducer vibrates the tip in a predictable, highly efficient vibration pattern of generally circular configuration, this pattern providing a highly effective wiping action at the tooth surface. In this and similar applications, the vibration frequency is maintained at about 25,000 cycles per second so that, in combination with water transmitted to the tip by the fluid delivery system, plaque and tartar are removed from the teeth surfaces in a highly effective manner. The vibration frequency, however, is maintained constant, even when the tip is pressed against the tooth surface with considerable force, thereby maintaining crystal vibration at or very near to the crystal resonant frequency within an optimum band width (Q). Consequently, the crystal is continuously driven at peak efficiency, and it does not tend to overheat. The water transmitted through the transducer to the tip, of course, further serves to cool the transducer, as well as the tip and the tooth enamel.

Although one preferred embodiment of the invention has been illustrated and described herein, variations will be apparent to one of ordinary skill in the art. Accordingly, the invention is not to be limited to the specific embodiment illustrated and described herein, and the true scope and spirit of the invention are to be determined by reference to the appended claims.

The embodiments of the invention in which an exclusive property or privilege is claimed are defined as follows:

1. An ultrasonic dental scaling tool connectable to an energizing system comprising:
    an elongated housing, and;
    a tubular piezo-electric transducer element within said housing responsive to an ultrasonic frequency electric signal for applying ultrasonic frequency vibrations to a replaceable hollow core work tool, and;
    means mounting said transducer element in said housing and providing for passage of a working fluid through said housing to said hollow core work tool comprising a tubular tension bolt extending axially through said transducer element, one end of said bolt being adapted for connection at a connection point with a hollow core work tool, and the other end being adapted for connection with a source of fluid such that the hollow fluid core of said bolt is communicatable with both the fluid source and the work tool hollow core, a seat on said tension bolt against which one end of said transducer element abuts and a reaction mass of high density material positioned by said bolt and compressively abutting the opposite end of said transducer element such that said transducer element is positioned on said bolt under compression, the transducer element seat being located with respect to the bolt work tool connection point such that a nodal point at the bolt work tool connection is provided, and a dielectric sheath on the bolt outer surface electrically insulating the bolt fluid core from said transducer element;
    source connection means connected to the housing for effecting connection to a source of a fluid and ultrasonic frequency electricity, and,
    further connecting means for connecting the hollow core of the bolt and the source connection means and the transducer element to the source connection means for providing a path for the fluid and ultrasonic electrical signal.

2. The dental system of claim 1, wherein said bolt includes a nut threadibly connected to said bolt, and said reaction mass means include a slotted ring shaped mass.

3. The dental system of claim 2, wherein said further connection means include a tubular member having an enlarged diameter portion which registers with the outline of said collar and intervening between said collar and said member for forming a fluid seal therebetween.

4. The dental system of claim 3, wherein said means intervening between said collar and said member is further operative for absorbing vibrational forces adjacent to the other end of said bolt.

5. The dental system of claim 1, wherein said bolt includes interior threads formed within a portion of said bolt adjacent to the one end thereof in co-axial relation with the bolt core.

6. The dental system of claim 1, wherein said sheat is a polytetrafioroetylene tube.

7. The dental system of claim 1, further including an energizing means comprising: a transformer with feedback, primary, and secondary windings each having two connections, and a transistor. The first connection of the primary winding of the transformer being effectively connected to a power supply and the second connection of the primary winding of the transformer being connected to the collector of the transistor; the secondary winding of the transformer being effectively connected to the transducer, the first connection of the feedback winding of the transformer being effectively connected to the base of the transistor and the second connection to the feedback winding of the transformer being effectively connected to ground for providing a control voltage for application to the base of the transistor for production of a condition responsive feedback network.

8. Dental means of claim 1, wherein the means for effectively connecting the feedback winding to ground is a timing network.

9. A dental system as in claim 1, wherein the means for effectively connecting the secondary of the transformer to the transducer includes means for varying the reactance to compensate for the variations in transducer reactance.

* * * * *